US006862096B2

(12) United States Patent
Vaez-Iravani et al.

(10) Patent No.: US 6,862,096 B2
(45) Date of Patent: Mar. 1, 2005

(54) DEFECT DETECTION SYSTEM

(75) Inventors: Mehdi Vaez-Iravani, Los Gatos, CA (US); Jeffrey Alan Rzepiela, Sunnyvale, CA (US); Carl Treadwell, Menlo Park, CA (US); Andrew Zeng, Milpitas, CA (US); Robert Fiordalice, Austin, TX (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 10/360,565

(22) Filed: Feb. 6, 2003

(65) Prior Publication Data

US 2003/0210393 A1 Nov. 13, 2003

Related U.S. Application Data

(62) Division of application No. 09/828,269, filed on Apr. 6, 2001, now Pat. No. 6,538,730.

(51) Int. Cl.$^7$ .............................................. G01B 11/30
(52) U.S. Cl. .................................. 356/600; 356/243.4
(58) Field of Search ........................... 356/237.1–237.6, 356/600–624, 243.1, 243.4, 392–394; 428/156, 161, 172

(56) References Cited

U.S. PATENT DOCUMENTS

| 4,314,763 A | 2/1982 | Steigmeier et al. |
| 4,378,159 A | 3/1983 | Galbraith |

(List continued on next page.)

FOREIGN PATENT DOCUMENTS

| JP | 63-14830 | 1/1988 |
| JP | 63-140904 | 6/1988 |
| JP | 62-85449 | 11/1998 |
| WO | 9615354 | 9/1996 |
| WO | WO 00/00873 | 1/2000 |
| WO | WO 00/00874 | 1/2000 |
| WO | WO 00/02037 | 1/2000 |

OTHER PUBLICATIONS

"Requirements for Future Surface Inspection Equipment for Bare Silicon Surfaces," P. Wagner et al., Wacker–Chemitronic GmbH, Burghausen, Germany, W. Baylies, BayTech Group, Weston Massachusetts.

(List continued on next page.)

*Primary Examiner*—Frank G. Font
*Assistant Examiner*—Sang H. Nguyen
(74) *Attorney, Agent, or Firm*—Parsons Hsue & de Runtz LLP

(57) ABSTRACT

Scattered radiation from a sample surface is collected by means of a collector that collects radiation substantially symmetrically about a line normal to the surface. The collected radiation is directed to channels at different azimuthal angles so that information related to relative azimuthal positions of the collected scattered radiation about the line is preserved. The collected radiation is converted into respective signals representative of radiation scattered at different azimuthal angles about the line. The presence and/or characteristics of anomalies are determined from the signals. Alternatively, the radiation collected by the collector may be filtered by means of a spatial filter having an annular gap of an angle related to the angular separation of expected pattern scattering. Signals obtained from the narrow and wide collection channels may be compared to distinguish between micro-scratches and particles. Forward scattered radiation may be collected from other radiation and compared to distinguish between micro-scratches and particles. Intensity of scattering is measured when the surface is illuminated sequentially by S- and P-polarized radiation and compared to distinguish between micro-scratches and particles. Representative films may be measured using profilometers or scanning probe microscopes to determine their roughness and by the above-described instruments to determine haze in order to build a database. Surface roughness of unknown films may then be determined by measuring haze values and from the database.

5 Claims, 10 Drawing Sheets

U.S. PATENT DOCUMENTS

| | | | |
|---|---|---|---|
| 4,391,524 A | | 7/1983 | Steigmeier et al. |
| 4,423,331 A | | 12/1983 | Koizumi et al. |
| 4,479,714 A | | 10/1984 | Lehrer |
| 4,508,450 A | | 4/1985 | Ohshima et al. |
| 4,523,841 A | | 6/1985 | Brunsting et al. |
| 4,526,468 A | | 7/1985 | Steigmeier et al. |
| 4,598,997 A | | 7/1986 | Steigmeier et al. |
| 4,735,504 A | | 4/1988 | Tycko |
| 4,744,663 A | | 5/1988 | Hamashima et al. |
| 4,794,265 A | | 12/1988 | Quackenbos et al. |
| 4,893,932 A | | 1/1990 | Knollenberg |
| 4,898,471 A | | 2/1990 | Stonestrom et al. |
| 4,929,845 A | | 5/1990 | Amir et al. |
| 5,076,692 A | | 12/1991 | Neukermans et al. |
| 5,108,176 A | | 4/1992 | Malin et al. |
| 5,189,481 A | | 2/1993 | Jann et al. |
| 5,198,869 A | * | 3/1993 | Monteverde et al. .... 356/243.4 |
| 5,218,417 A | * | 6/1993 | Gay et al. ................... 356/300 |
| 5,270,794 A | | 12/1993 | Tsuji et al. |
| 5,315,609 A | | 5/1994 | Tanaka et al. |
| 5,377,001 A | | 12/1994 | Malin et al. |
| 5,377,002 A | | 12/1994 | Malin et al. |
| 5,389,794 A | | 2/1995 | Allen et al. |
| 5,406,367 A | | 4/1995 | Sopori |
| 5,416,594 A | | 5/1995 | Gross et al. |
| 5,424,838 A | | 6/1995 | Siu |
| 5,464,779 A | * | 11/1995 | Fujimaki ..................... 438/16 |
| 5,530,550 A | | 6/1996 | Nikoonahad et al. |
| 5,650,614 A | | 7/1997 | Yasutake et al. |
| 5,677,765 A | * | 10/1997 | Laird et al. ............... 356/237.5 |
| 5,744,215 A | * | 4/1998 | Neuman ..................... 428/141 |
| 5,798,829 A | | 8/1998 | Vaez-Iravani et al. |
| 5,798,831 A | | 8/1998 | Hagiwara |
| 5,864,394 A | | 1/1999 | Jordan, III et al. |
| 6,104,945 A | | 8/2000 | Modell et al. |
| 6,201,601 B1 | | 3/2001 | Vaez-Iravani et al. |
| 6,271,916 B1 | | 8/2001 | Marxer et al. |
| 6,538,730 B2 | | 3/2003 | Vaez-Iravani et al. |

OTHER PUBLICATIONS

"The Importance of Media Refractive Index in Evaluating Liquid and Surface Microcontamination Measurements," R. Knollenberg et al., *The Journal of Environmental Sciences*, Mar./Apr. 1987.

"Surface Inspection System for Estimation of Wafer," Y. Yatsugake et al., *Hitachi Engineering Technical Report*, vol. 11, Jan. 1996, pp. 21–26 (with translation).

Figure, Hitachi Electronics Engineering Co., Ltd., presented by Etsuro Morita of Mitsubishi Materials Silicon Corp. in a presentation entitled "Exploration of COP and COP Defect Crystal Originated 'Particles'." at the $6^{th}$ International Workshop on 300 mm wafers on Dec. 5, 1996 in Makuhari. Japan.

* cited by examiner

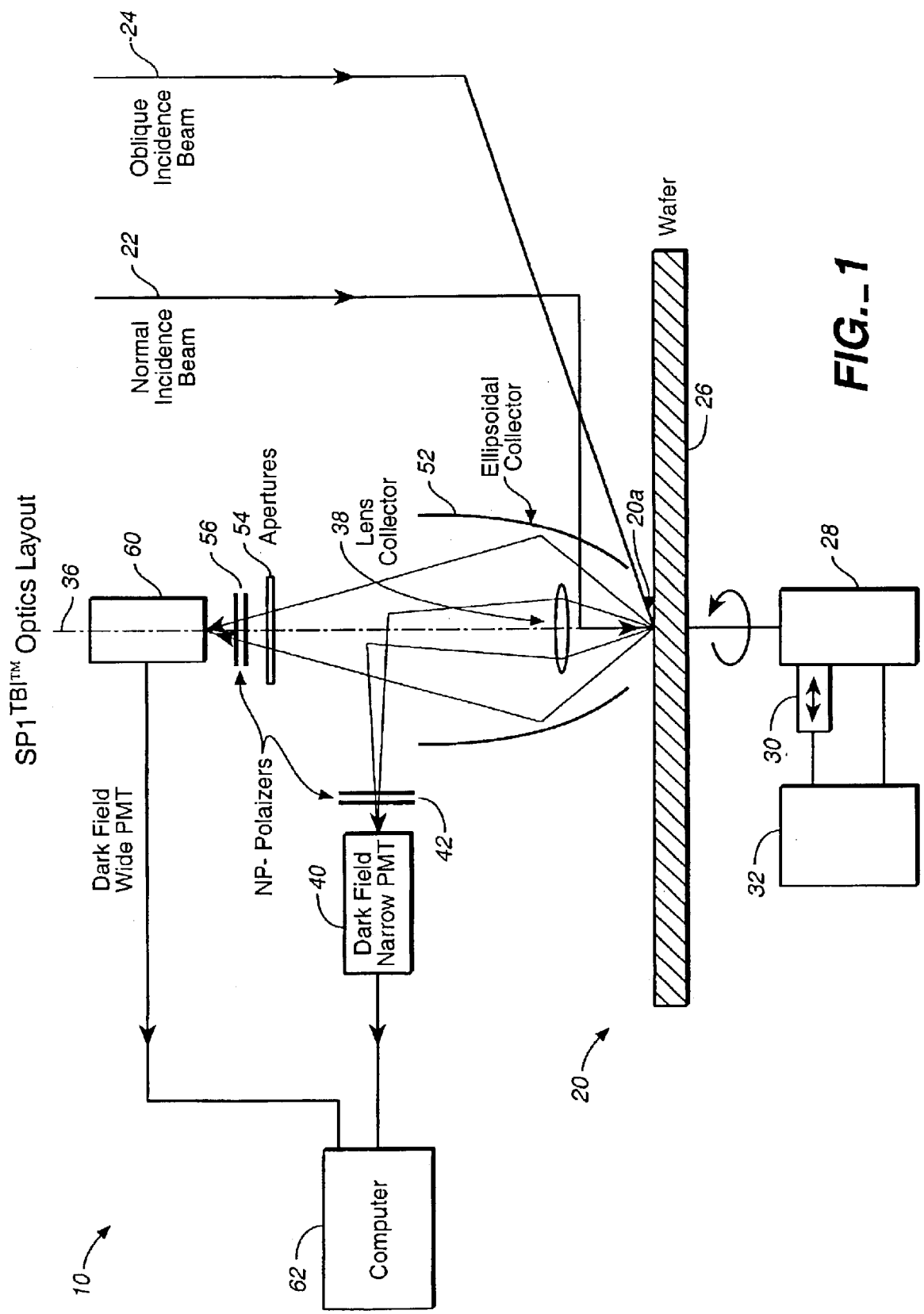
FIG._1

Convergent Hollow Cone of Light
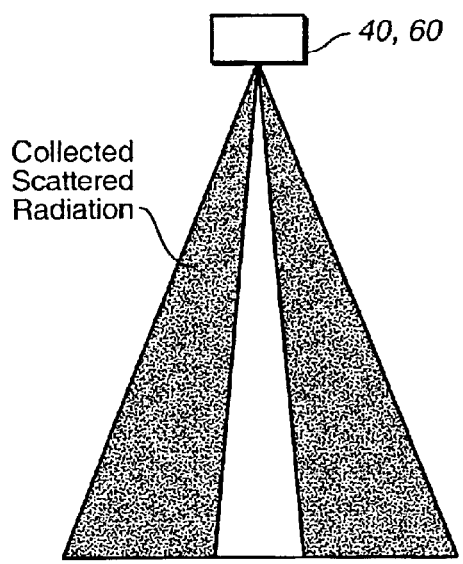
FIG._2
A Possible Arrangement of Multiple Fiber Channels
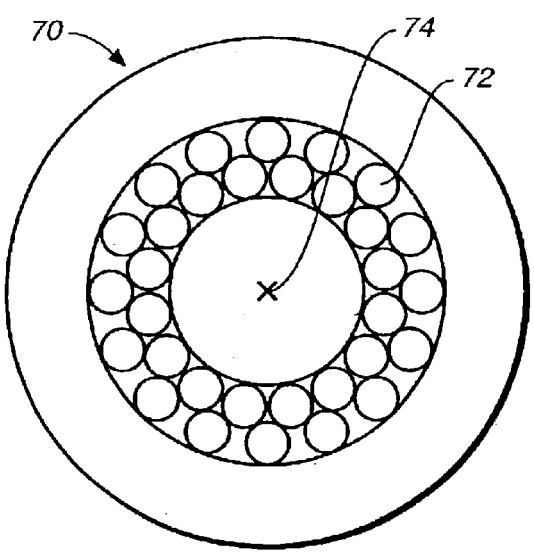
FIG._3A
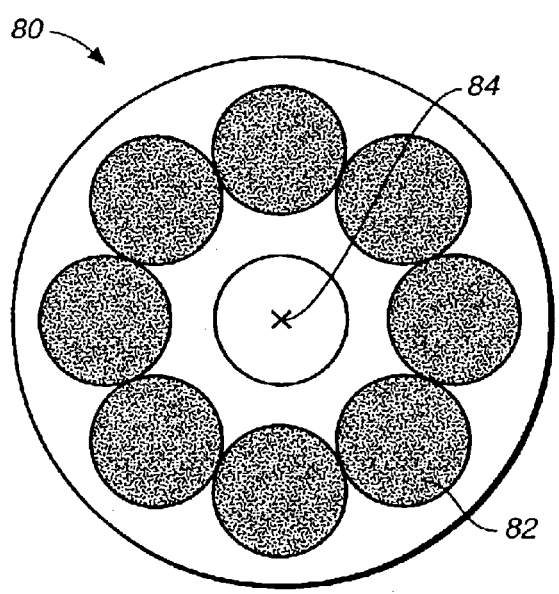
FIG._4
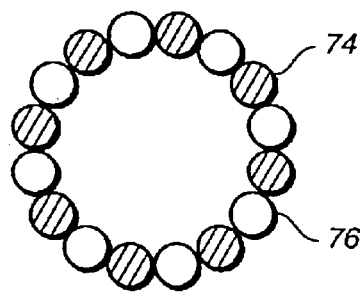
FIG._3B

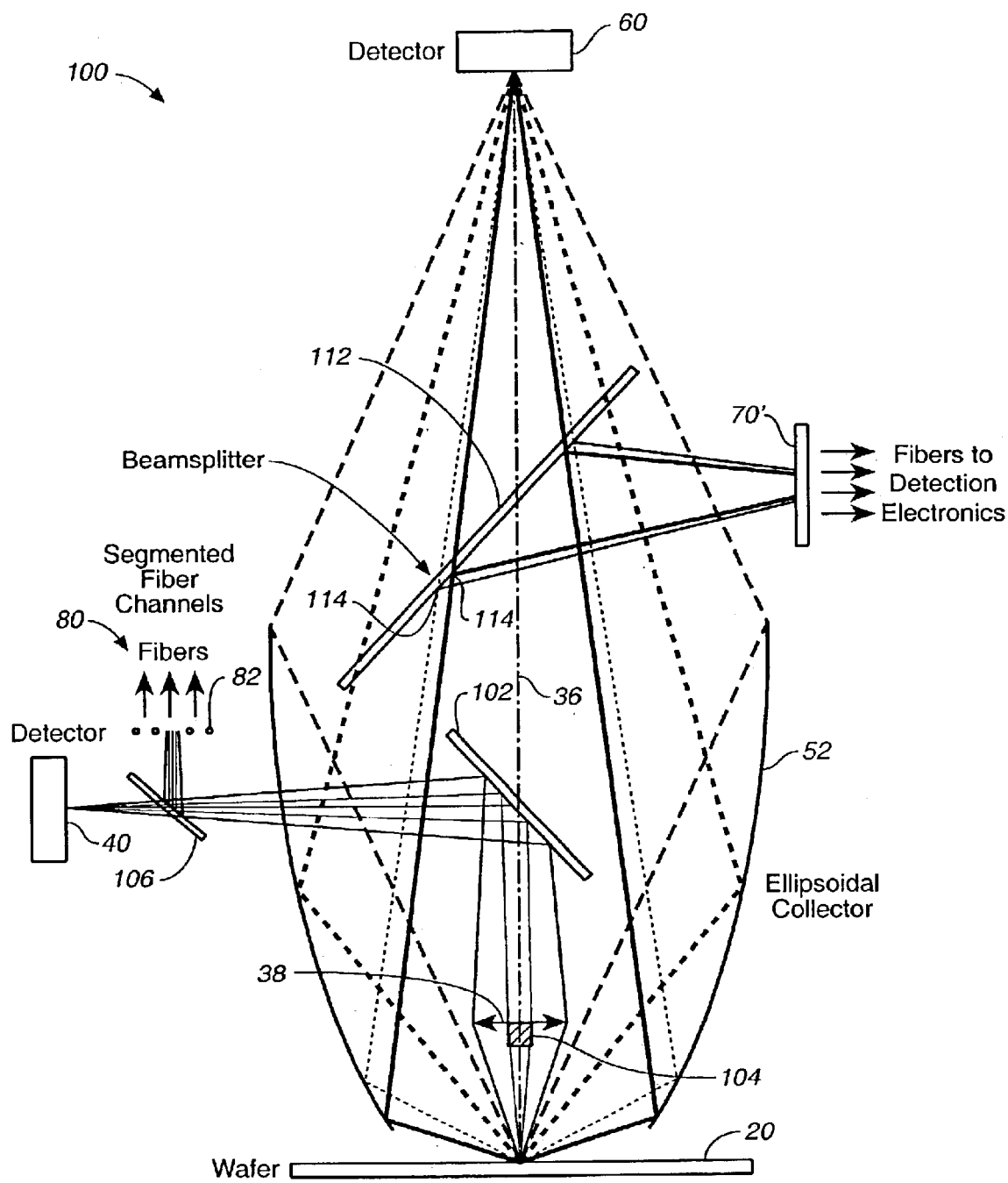
FIG._5A
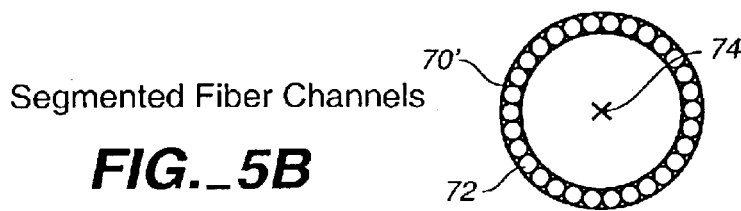
FIG._5B

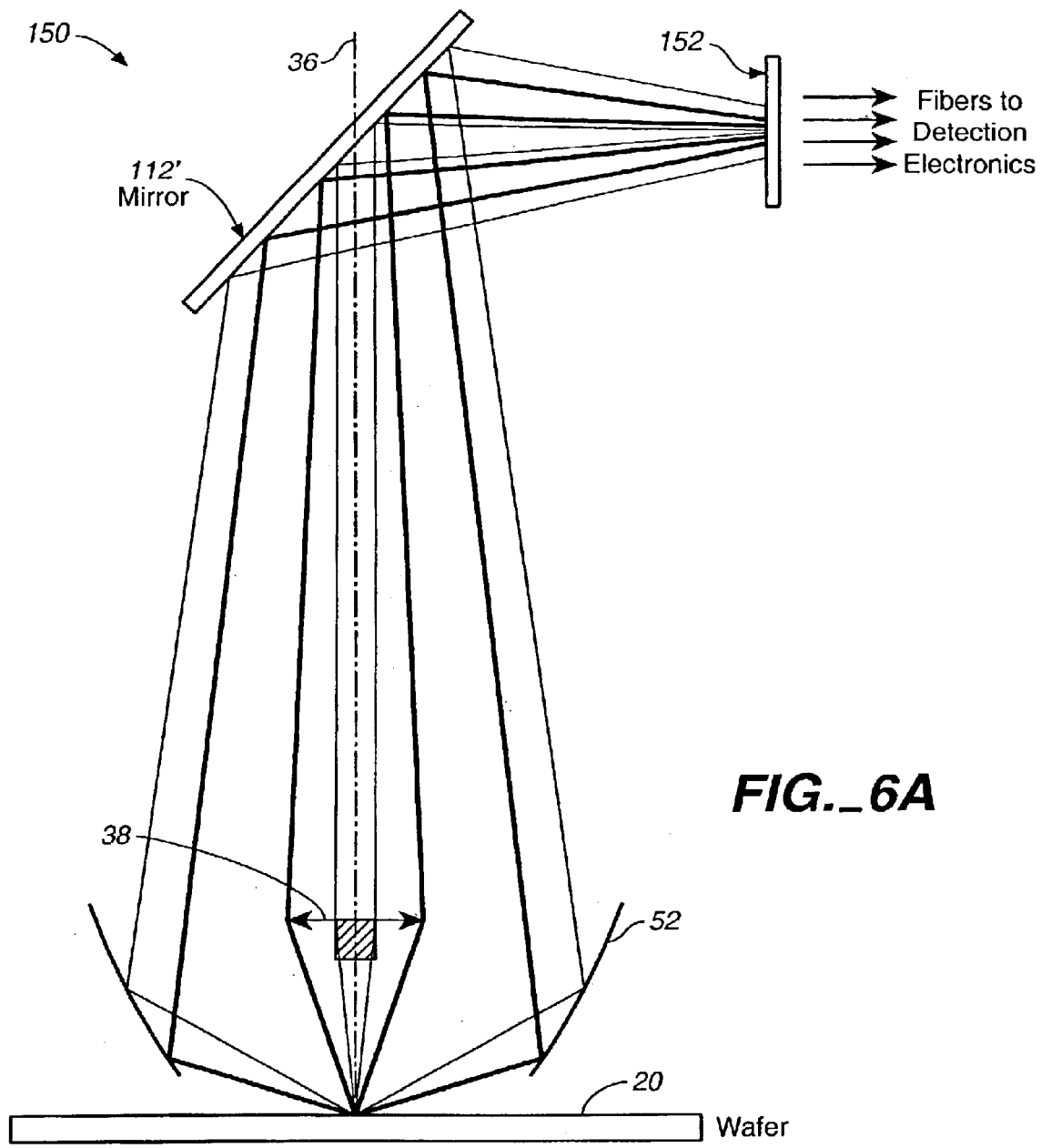
FIG._6A
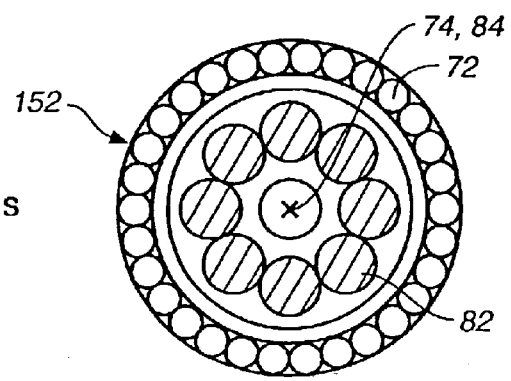
Segmented Fiber Channels
FIG._6B

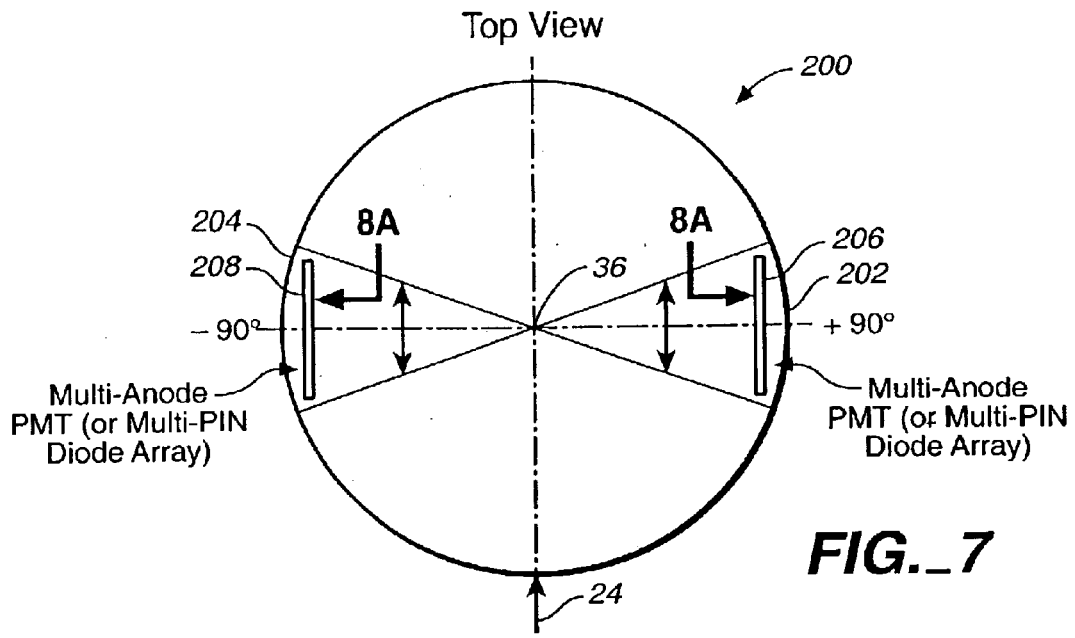
FIG._7
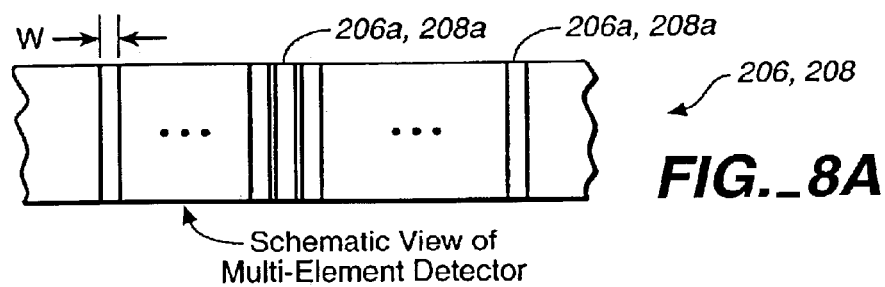
FIG._8A
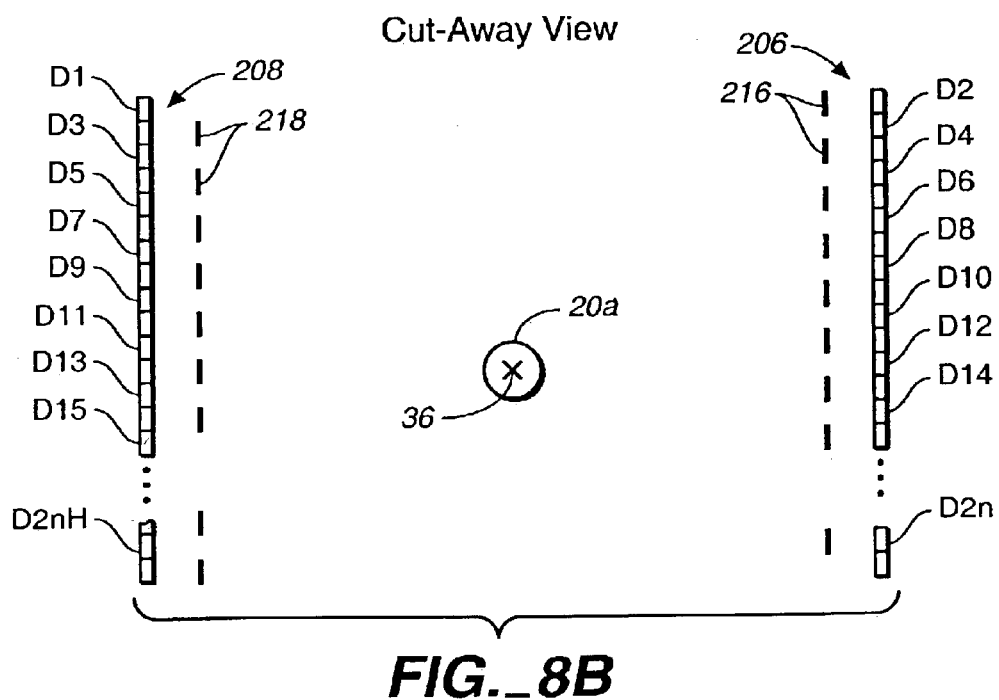
FIG._8B

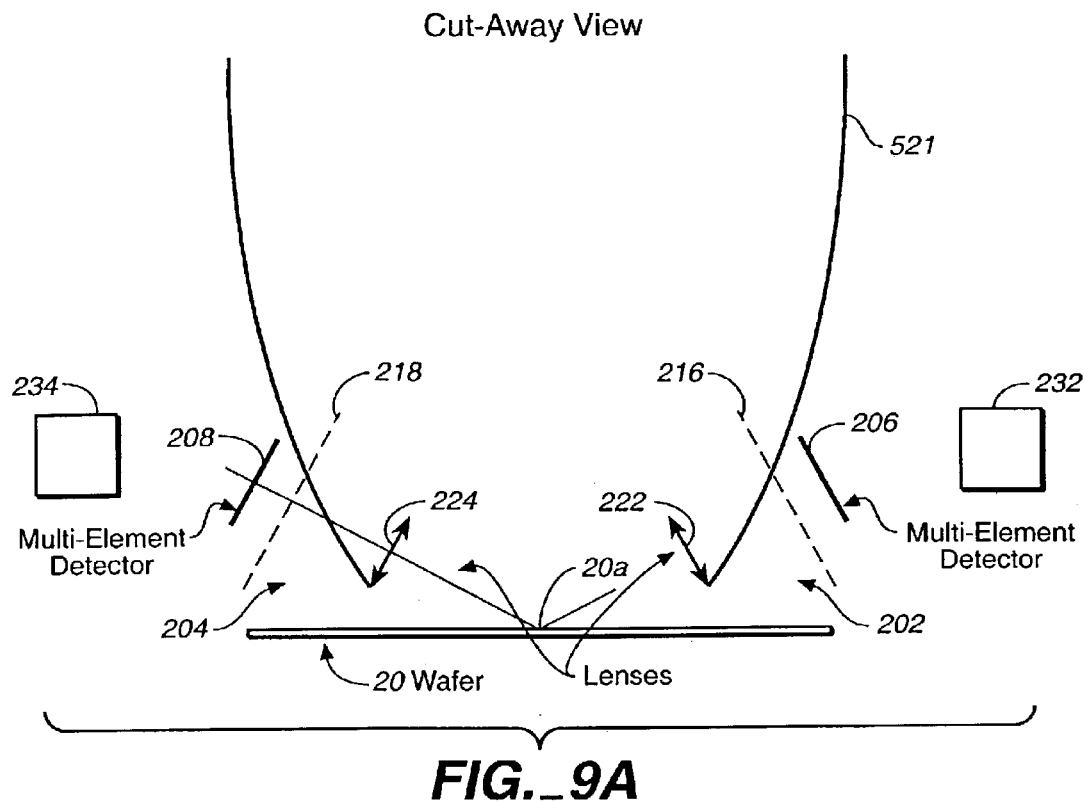
FIG._9A
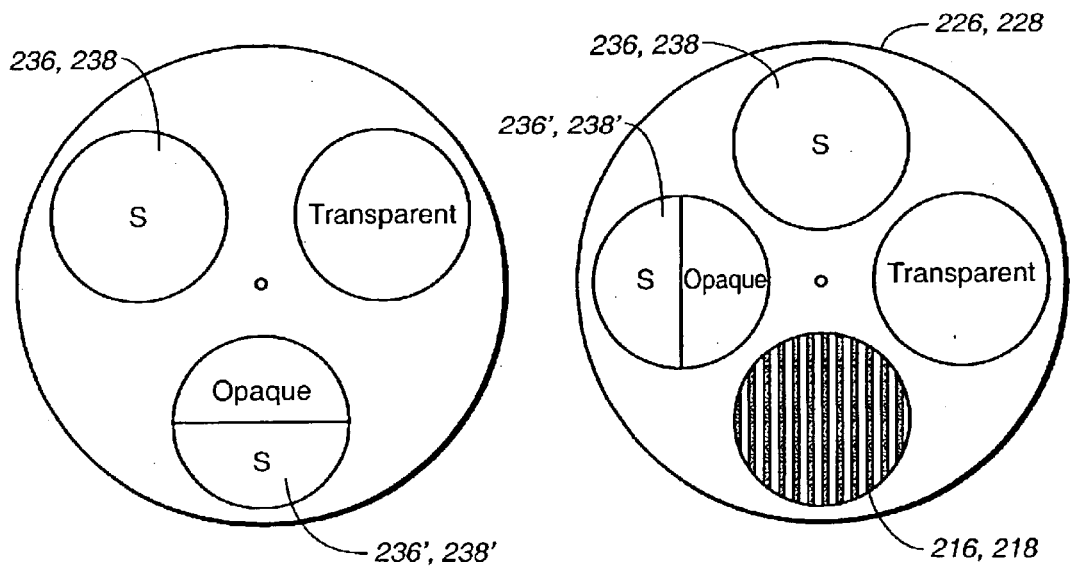
FIG._9C  FIG._9B

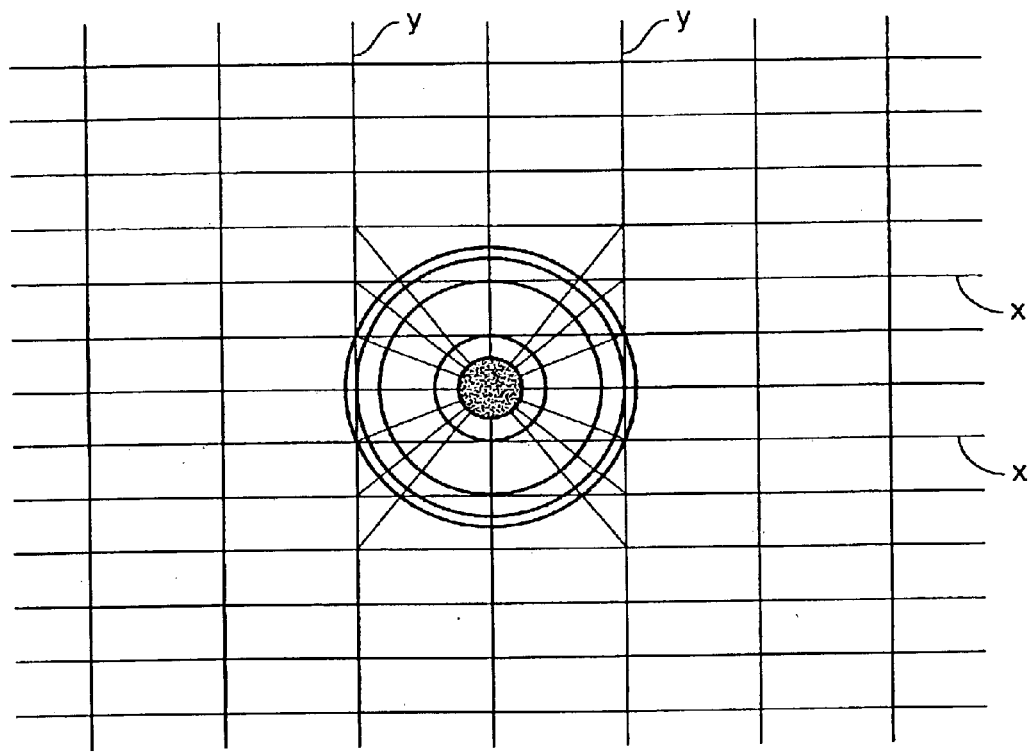
FIG._10
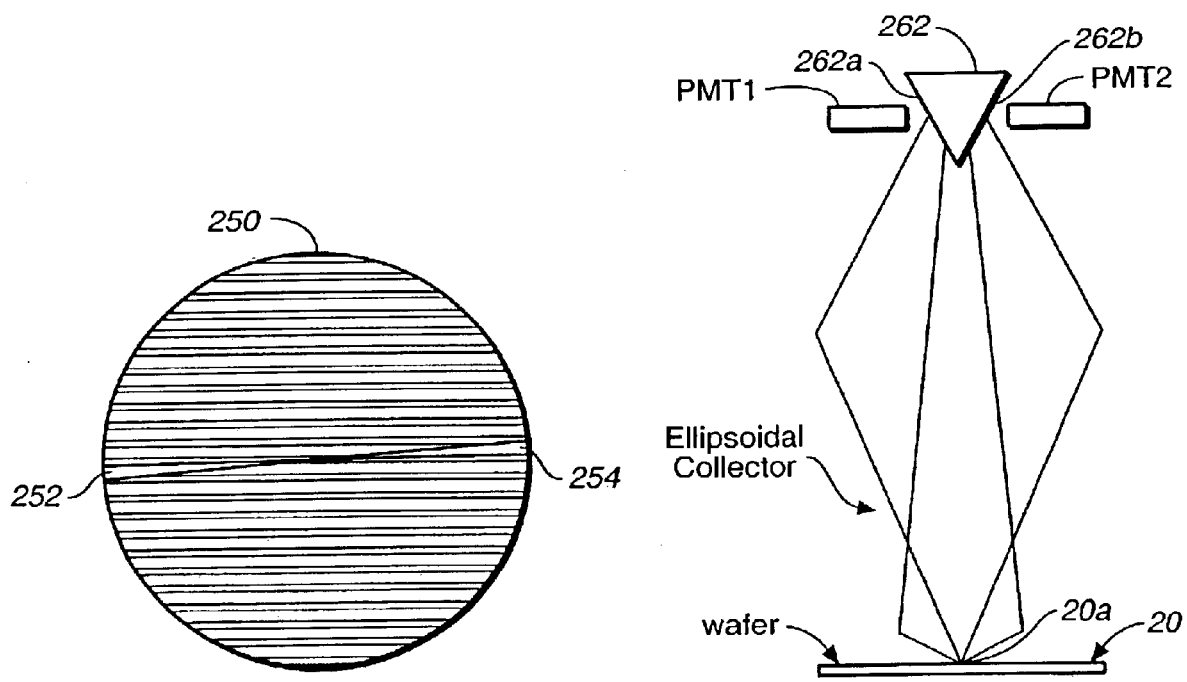
FIG._11  FIG._12

Aperture 1
90° Opening in Forward Direction
Aperture 2
90° Blocked in Forward Direction
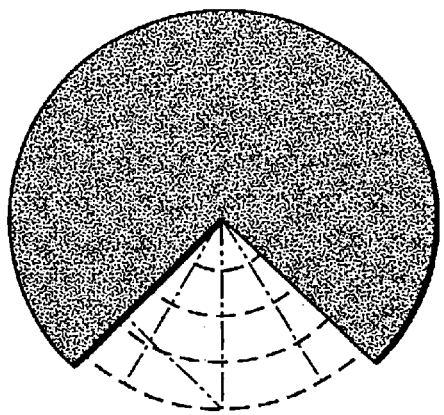
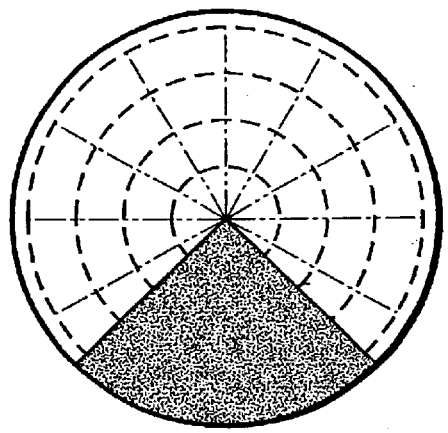
*FIG._13A*
*FIG._13B*
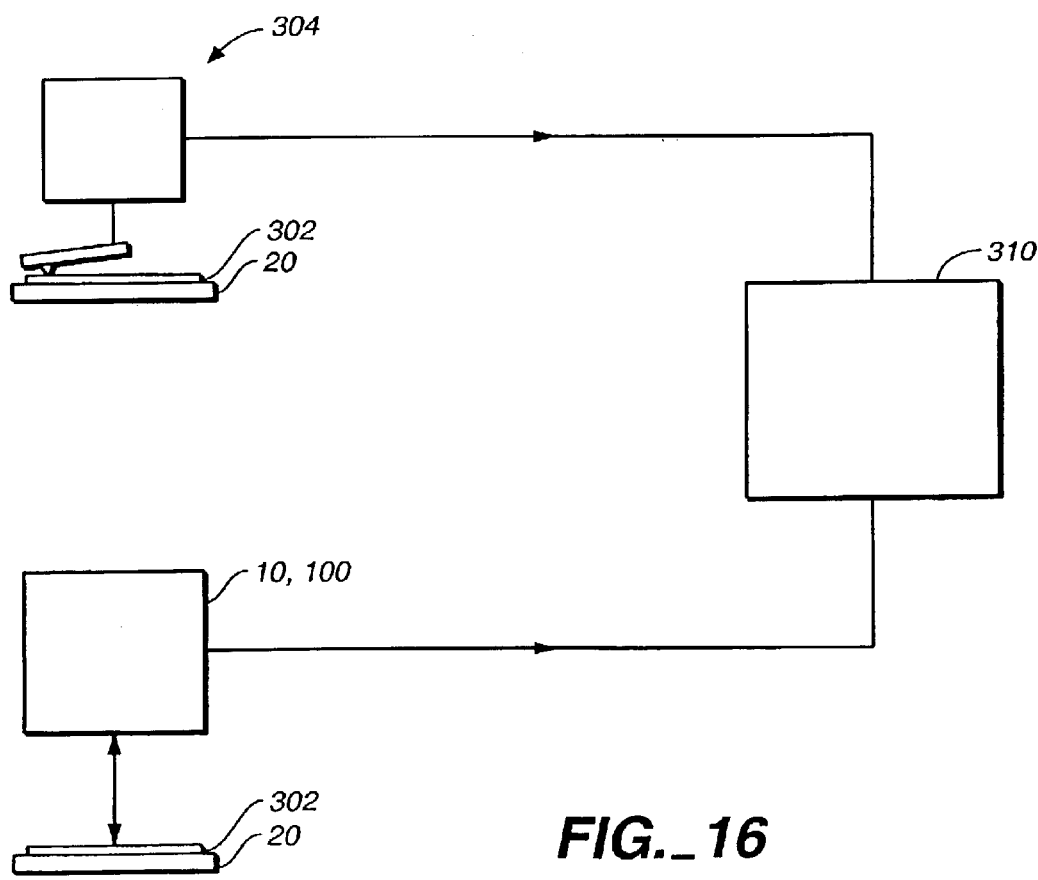
*FIG._16*

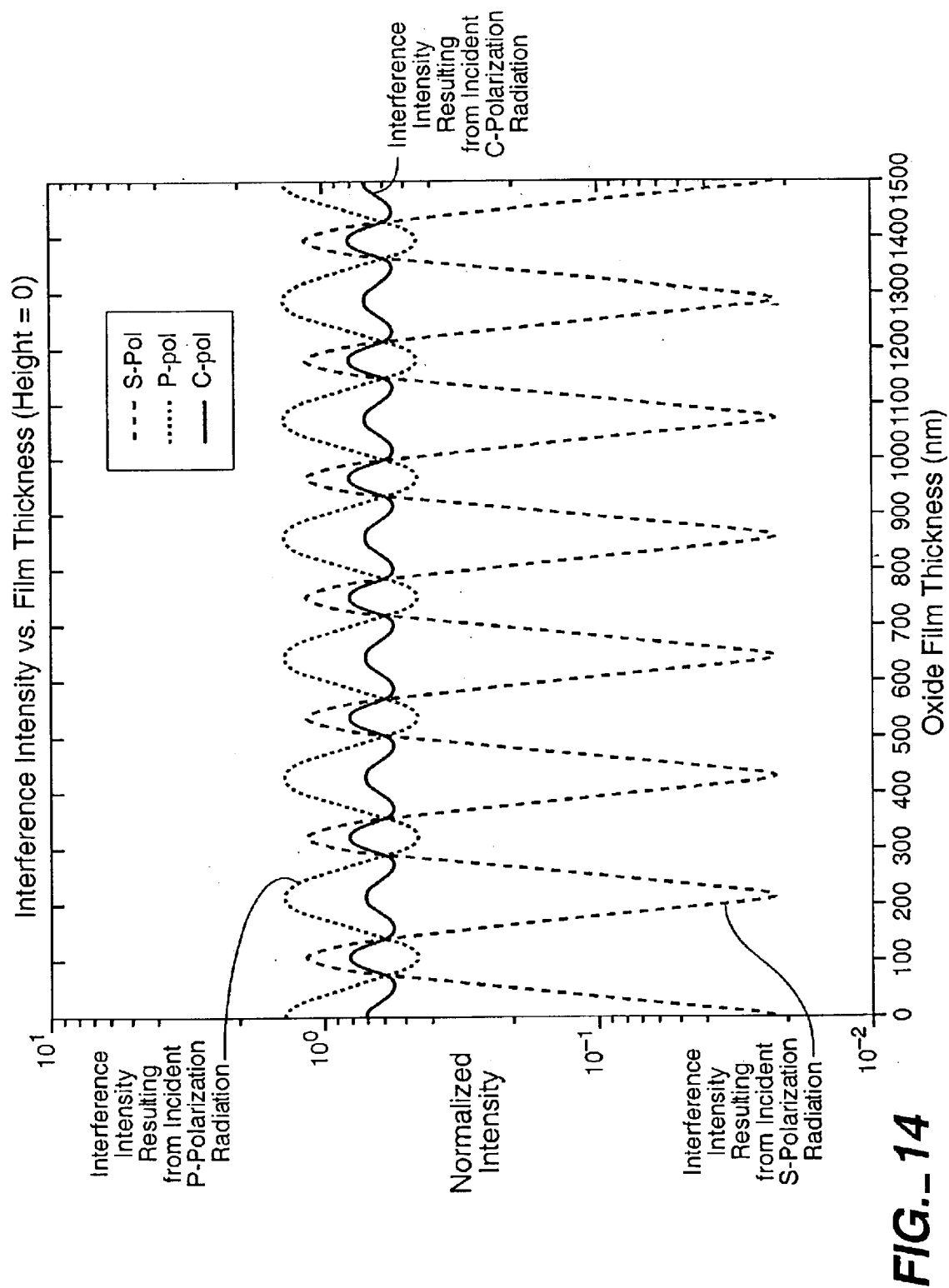
FIG._14

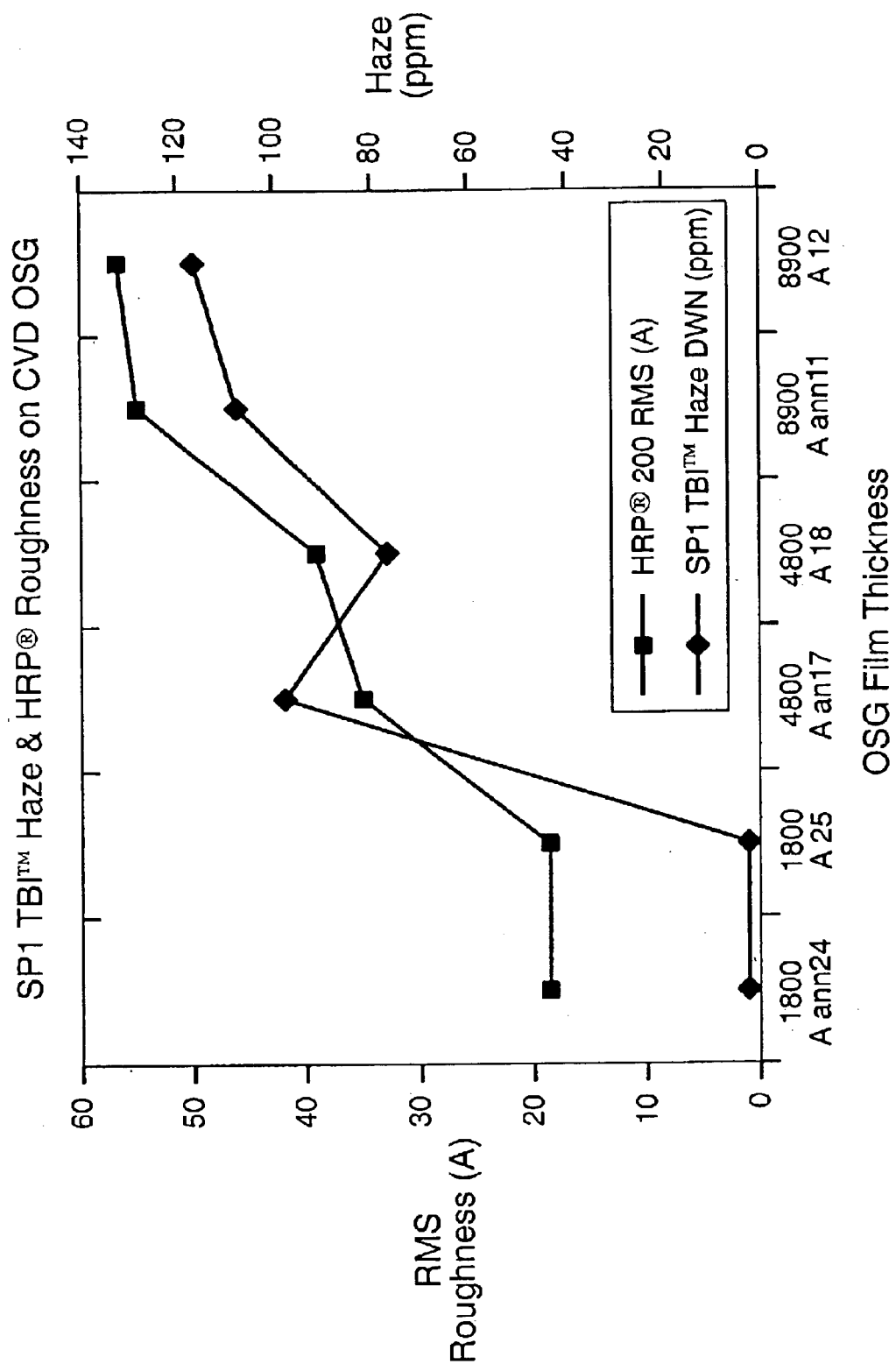
FIG._15

DEFECT DETECTION SYSTEM

This is a division of application Ser. No. 09/828,269 filed Apr. 6, 2001, now U.S. Pat. No. 6,538,730.

CROSS REFERENCE TO RELATED APPLICATION

This application is related to U.S. patent application Ser. No. 08/770,491, filed Dec. 20, 1996, U.S. Pat. No. 6,201,601, issued Mar. 13, 2001 and the application being filed concurrently herewith. The related applications and the issued patent are incorporated herein by reference in their entireties.

BACKGROUND OF THE INVENTION

This invention relates in general to defect detection, and, in particular, to an improved system for detecting anomalies on surfaces, such as particles and surface-originated defects such as crystal-originated particles ("COPs"), surface roughness and micro-scratches.

The SP1$^{TBI}$™ detection system available from KLA-Tencor Corporation of San Jose, Calif., the Assignee of the present application, is particularly useful for detecting defects on unpatterned semiconductor wafers. While the SP1$^{TBI}$ system provides unsurpassed defect sensitivity on bare wafers or unpatterned wafers, this is not the case when it is used for inspecting wafers with patterns thereon such as wafers with memory arrays. In this system, all of the radiation collected by a lens or ellipsoidal mirror is directed to a detector to provide a single output. Thus, since pattern on the wafer will generate Fourier and/or other strong scattering signals, when these signals are collected and sent to the detector, the single detector output becomes saturated and unable to provide information useful for detecting defects on the wafer.

Conventional techniques for detecting defects on wafers are either tailored for the inspection of patterned wafers, or for inspecting unpatterned or bare wafers, but not both. While inspection systems for detecting patterned wafers may be also used for inspecting unpatterned wafers, such systems are typically not optimized for such purposes. Systems designed for the inspection of unpatterned or bare wafers, on the other hand, may have difficulties handling the diffraction or other scattering caused by the patterned structures on patterned wafers, for reasons such as those explained above.

For the inspection of patterned wafers, entirely different inspection systems have been employed. One commercial system, known as AIT™ inspection system, is available from the Assignee of the present application, KLA-Tencor Corporation of San Jose, Calif.; such system is also described in a number of patents, including U.S. Pat. No. 5,864,394. In the AIT system, spatial filters are employed to shield the detectors from the diffraction or scattering from the patterned structures on the wafer. The design of such spatial filters can be based on prior knowledge of the patterned structures and can be quite complex. Furthermore, this system utilized a die to die comparison process in order better to identify the presence of a defect.

None of the above-described instruments is entirely satisfactory for the inspection of patterned wafers. It is therefore desirable to provide an improved defect detection system for patterned wafers in which the above difficulties are alleviated. To further economize on the space required for inline inspection, it is desirable to provide an instrument that can be optimized for both unpatterned and patterned wafer inspection.

Chemical mechanical planarization (CMP) has gained wide acceptance in the semiconductor industry. The CMP process, however, also creates many types of defects that can significantly impact the yield of an integrated circuit (IC) device if the defects are not properly controlled. Among the CMP defects, the micro-scratch has a strong impact on IC yield. Therefore, it is desirable to be able to detect and differentiate micro-scratches and other CMP defects from particles.

One important parameter for monitoring the quality of unpatterned or bare films on silicon wafers is the surface roughness. Surface roughness is typically measured by an instrument such as the HRP® instruments from KLA-Tencor Corporation, the Assignee of the present application, or by means of other instruments such as atomic force microscopes or other types of scanning probe microscopes such as scanning tunneling microscopes. One disadvantage of such instruments is the slow speed of their operation. It is therefore desirable to provide an alternative system which may be used for giving a measure of surface roughness at a speed much faster than the above-described instruments.

SUMMARY OF THE INVENTION

One aspect of the invention is based on the observation that the collectors in the SP1$^{TBI}$ instruments preserve the azimuthal information of the scattered radiation by the surface inspected. Thus, by segmenting and directing the scattered radiation collected by the type of collectors used in the SP1$^{TBI}$ instruments at different azimuthal positions to separate collection channels, the above-described difficulties are overcome so that an instrument may be constructed which is also optimized for the detection of patterned wafers. In this manner, a compact instrument can be achieved for measuring defects of patterned wafers. In addition to the ellipsoidal mirror used in the SP1$^{TBI}$ instruments, other azimuthally symmetric collectors may be used, such as a paraboloidal mirror used together with one or more lenses.

As in the SP1$^{TBI}$ system, the surface inspection system of one aspect of this invention collects radiation scattered from the surface by means of a collector that collects scattered radiation substantially symmetrically about a line normal to the surface. By directing to different channels the collected radiation scattered at different azimuthal angles about the line or another direction, these channels will carry information related to scattered radiation at corresponding relative azimuthal positions of the scattered radiation. Preferably, the channels are separated from each other by separators to reduce cross-talk. The collected scattered radiation carried by at least some of the channels may then be used for determining the presence and/or characteristics of anomalies in or on the surface. In addition, the multiple views of the same event can significantly facilitate the process of real time defect classification (RTDC).

In the above-described scheme, if only a portion of the collected radiation is directed to the different channels, while another portion of the collected radiation at different azimuthal angles are directed to a single detector for providing a single output as in the conventional SP1$^{TBI}$ scheme, the system can then be used for inspecting both unpatterned and patterned wafers. In other words, if the SP1$^{TBI}$ scheme is modified by diverting a portion of the collected radiation in the manner described above to different channels while preserving azimuthal information, a versatile tool results that can be optimized for the inspection of both unpatterned and patterned wafers. In this manner, semiconductor manufacturers no longer have to employ two different tools, each optimized for the detection of patterned or unpatterned wafers.

In the above-described scheme, since collected radiation at different azimuthal angles about the line normal to the surface are directed to different collection channels and converted into separate signals, the signals containing pattern diffraction can be discarded and the remaining signals not containing pattern scatter may then be used for the detection and classification of anomalies in or on the surface of the wafer. While the above-described systems are particularly useful for the inspection of semiconductor wafers, they can also be used for he inspection of anomalies on other surfaces such as flat panel displays, magnetic heads, magnetic and optical storage media and other applications.

Another aspect of the invention is based on the observation that the radiation collected by a collector (such as the one described above) may be filtered by means of a spatial filter having an angular gap of an angle related to the angular separation of expected radiation components scattered by pattern on the surface. In this manner, the filtered radiation at some relative positions of the surface relative to the filter will contain information concerning defects of surfaces unmasked by pattern scattering that would interfere with the measurements. When such radiation is detected by the detectors, the detector outputs can then be used for detecting the presence and/or characteristics of anomalies in or on the surface.

The SP1$^{TBI}$ tool or the above-described systems may be used for distinguishing between particles and micro-scratches caused by CMP. Scattered radiation along directions close to the normal direction is collected by a first detector and radiation scattered along directions away from the normal direction is collected by a second detector. A ratio is then derived from the outputs of the two detectors to determine whether an anomaly on the surface is a micro-scratch or a particle.

The CMP micro-scratches tend to scatter radiation from an oblique incident beam in the forward direction while particles tend to scatter such radiation more evenly. Radiation scattered by the surface along forward scattering directions is collected separately from scattered radiation in other scattering directions. Two different signals are derived from the separately collected scattered radiation and compared for determining whether an anomaly on the surface is a micro-scratch or particle.

In another aspect of the invention, an S-polarized radiation beam and a P-polarized radiation beam are provided sequentially in oblique direction(s) to the surface during two different scans of the surface. The radiation scattered by a defect during the first and second scans is collected to provide a pair of signals indicative of the scattered radiation of two different incident polarizations. The pair of signals is then compared to a reference to determine whether an anomaly on the surface is a micro-scratch or particle.

In order to speed up the process for determining the surface roughness of thin films, a database correlating haze values with surface roughness of thin films is provided. The haze value of the surface is then measured by a tool such as the SP1$^{TBI}$ or one of the above-described systems, and a roughness value of the surface may then be determined from the measured haze value and the database. For example, the database may be compiled by means of a tool such as the SP1$^{TBI}$ or one of the above-described systems for measuring the haze values of representative thin films and another tool such as an HRP® profiler or other type of profilometer or a scanning probe microscope for measuring the surface roughness of such films.

Any one of the above-described aspects of the invention may be used individually or in any combination to achieve the advantages described herein.

BRIEF DESCRIPTION OF THE DRAWINGS

FIG. 1 is a schematic diagram of the SP1$^{TBI}$ system useful for illustrating the invention.

FIG. 2 is a schematic diagram illustrating a convergent hollow cone of radiation to illustrate one aspect of the invention.

FIG. 3A is a schematic view of a possible arrangement of multiple fiber channels for carrying scattered radiation collected by the ellipsoidal collector of the system of FIG. 1 to illustrate one aspect of the invention.

FIG. 3B is a schematic view of an multi-anode photomultiplier tube (PMT) that can be used in conjunction with an arrangement of multiple fiber channels such as that shown in FIG. 3A to illustrate one aspect of the invention.

FIG. 4 is a schematic view of an arrangement of fiber channels/multiple detectors for carrying scattered radiation collected by the lens collector in the narrow channel of the system of FIG. 1 to illustrate an aspect of the invention.

FIG. 5A is a cross-sectional view of a defect inspection system to illustrate the preferred embodiment of the invention.

FIG. 5B is a cross-sectional view of an arrangement of separate optical channels used in the embodiment of FIG. 5A.

FIG. 6A is a cross-sectional view of a defect inspection system to illustrate an alternative embodiment of the invention.

FIG. 6B is a cross-sectional view of an arrangement of segmented optical channels used in the embodiment of FIG. 6A.

FIG. 7 is a top view of a portion of a defect inspection system to illustrate another alternative embodiment of the invention.

FIG. 8A is a schematic view of a multi-element detector in the embodiment of FIG. 7.

FIG. 8B is a schematic view of two multi-element detectors for use in the embodiment of FIG. 7.

FIG. 9A is a partly cross-sectional and partly schematic view of a defect inspection system to illustrate yet another alternative embodiment of the invention.

FIGS. 9B and 9C are schematic views of filter wheels useful in the embodiment of FIG. 9A.

FIG. 10 is a schematic view of a two-dimensional diffraction components from a pattern on a surface to be inspected illustrating an aspect of the invention.

FIG. 11 is a schematic view of a defect inspection system to illustrate one more alternative embodiment of the invention.

FIG. 12 is a schematic view of an asymmetric mask for use in the different embodiments of this invention.

FIGS. 13A and 13B are schematic views of two masks used with the different systems of this application to illustrate yet another aspect of the invention.

FIG. 14 is a graphical plot of the interference intensity of thin film surfaces when illuminated with radiation of three different polarizations to illustrate another aspect of the invention.

FIG. 15 is a graphical plot of haze and surface roughness to illustrate yet another aspect of the invention.

FIG. 16 is a block diagram illustrating a system measuring surface roughness and haze of representative films for compiling a database useful for the invention of FIG. 15.

For simplicity in description, identical components are identified by the same numerals in this application.

DETAILED DESCRIPTION OF THE EMBODIMENTS

FIG. 1 is a schematic view of the SP1$^{TBI}$ system 10 available from KLA-Tencor Corporation of San Jose, Calif., the assignee of the present application. Aspects of the SP1$^{TBI}$ system 10 are described in U.S. patent application Ser. No. 08/770,491, filed Dec. 20, 1996 and U.S. Pat. No. 6,201,601, both of which are incorporated in their entireties by reference. To simplify the figure, some of the optical components of the system have been omitted, such as components directing the illumination beams to the wafer. The wafer 20 inspected is illuminated by a normal incidence beam 22 and/or an oblique incidence beam 24. Wafer 20 is supported on a chuck 26 which is rotated by means of a motor 28 and translated in a direction by gear 30 so that beams 22 and/or 24 illuminates an area or spot 20a which is caused to move and trace a spiral path on the surface of wafer 20 to inspect the surface of the wafer. Motor 28 and gear 30 are controlled by controller 32 in a manner known to those skilled in the art. Alternatively, the beam(s) 22, 24 may be caused to move in a manner known to those skilled in the art to trace the spiral path or another type of scan path.

The area or spot 20a illuminated by either one or both beams on wafer 20 scatters radiation from the beam(s). The radiation scattered by area 20a along directions close to a line 36 perpendicular to the surface of the wafer and passing through the area 20a is collected and focused by lens collector 38 and directed to a PMT 40. Since lens 38 collects the scattered radiation along directions close to the normal direction, such collection channel is referred to herein as the narrow channel and PMT 40 as the dark field narrow PMT. When desired, one or more polarizers 42 may be placed in the path of the collected radiation in the narrow channel.

Radiation scattered by spot 20a of wafer 20, illuminated by either one or both beams 22, 24, along directions away from the normal direction 36 is collected by an ellipsoidal collector 52 and focused through an aperture 54 and optional polarizers 56 to dark field PMT 60. Since the ellipsoidal collector 52 collects scattered radiation along directions at wider angles from the normal direction 36 than lens 38, such collection channel is referred to as the wide channel. The outputs of detectors 40, 60 are supplied to a computer 62 for processing the signals and determining the presence of anomalies and their characteristics.

The SP1$^{TBI}$ system is advantageous for unpatterned wafer inspection since the collection optics (lens 38 and mirror 52) is rotationally symmetric about the normal direction 36, so that the orientation of the system in FIG. 1 relative to the orientation of defects on the surface of wafer 20 is immaterial. In addition, the angular coverage of the scattering space by these collectors is well matched to those required to detect the anomalies of interest in unpatterned wafer inspection applications.

In addition to the above characteristic, however, the SP1$^{TBI}$ system 10 has another important characteristic in that both its lens collector 38 and the ellipsoidal mirror collector 52 preserve the azimuthal information contained in radiation scattered by defects on surface of wafer 20. Thus, certain defects and/or pattern on the wafer may scatter radiation preferentially along certain azimuthal directions more than other azimuthal directions. By making use of the preserved azimuthal information in the collected radiation by the collectors 38 and 52, system 10 may be advantageously adapted and modified for the detection of defects on patterned wafers.

One aspect of the invention is based on the recognition that, by segmenting the radiation collected by the lens 38 and/or ellipsoidal mirror 52, radiation scattered in different azimuthal directions may be detected separately. In this manner, the detectors detecting radiation diffracted or scattered by pattern may become saturated, while other detectors not detecting such diffraction or scatter will yield useful signals for the detection and classification of defects on wafer 20. Since the lens 38 and ellipsoidal mirror 52 preserve the azimuthal information of the scattered radiation, knowledge of the type of pattern or defects present on wafer 20 can be advantageously used to design and position multiple detectors to advantageously detect and classify the defects on the wafer. This is especially true in the case of regular patterns such as memory structures on wafer 20, as will be explained below, since radiation diffracted by such regular patterns also tend to be regular.

FIG. 2 is a schematic view illustrating a convergent hollow cone of radiation which can be collected by lens 38 or mirror 52. In the case of lens 38 of FIG. 1, a spatial filter (not shown in FIG. 1) is employed to block the specular reflection of the normal incidence beam 22 from reaching detector 40, so that the radiation focused by lens 38 to PMT 40 has the shape of a convergent hollow cone illustrated in FIG. 2. In the case of the ellipsoidal mirror 52, since the mirror is not a complete ellipse, it collects only radiation scattered at larger angles to the normal direction 36 without also collecting the radiation scattered at near normal directions, so that the radiation focused by mirror 52 towards detector 60 also has the shape of a convergent hollow cone as shown in FIG. 2.

FIG. 3A is a schematic view of a possible arrangement of multiple fiber channels receiving radiation in the convergent cone of radiation shown in FIG. 2, such as that collected by mirror 52, to illustrate the preferred embodiment of the invention. The arrangement in FIG. 3A comprises two substantially concentric rings of optical fiber channels 72 that are used to carry the collected scattered radiation in the convergent hollow cone shown in FIG. 2. Fourier components or other pattern scattering from the pattern on the wafer 20 may reach some of the fibers 72, thereby causing the detectors detecting the radiation from such channels to be saturated. However, there will be other optical fiber channels that do not receive such unwanted pattern scattering. The use of multiple fiber channels 72 effectively segments the collected scattered radiation into different sectors or segments so that only some of the fiber channels will receive a strong signal and can become saturated due to the Fourier or other pattern scatter leaving the remaining channels carrying information that can be analyzed for detecting anomalies. As will be explained below, since the azimuthal information in the collected scattered radiation in the cone of FIG. 2 is preserved, various schemes may be employed to minimize the effects of the pattern scatter when the segmented approach of FIG. 3A is used.

Different types of detectors may be used to detect the radiation carried by the fiber channels 72, such as the multi-anode PMT shown in FIG. 3B. In the event multi-anode PMT is used, however, there is a nominal three percent cross-talk between any two adjacent channels. To avoid such cross-talk, fibers 72 may be aligned with every other PMT anode, in a manner illustrated in FIG. 3B. FIG. 3B is a schematic view of a multi-anode PMT. As shown in FIG. 3B, only the anodes 74 that are shaded are aligned with fibers 72, where anodes 76 are not aligned with any of the fibers 72. This avoids the three percent cross-talk that may be present if all of the anodes shown in FIG. 3B are aligned with fibers 72.

FIG. 4 is a schematic view illustrating an arrangement 80 of fiber channels or multiple detectors 82 for the narrow channel. Thus, fibers or detectors 82 may be aligned with the collected scattered radiation illustrated in FIG. 2 for the narrow channel collected by lens 38 for segmenting the radiation in a similar manner as that described above for the wide channel.

FIG. 5A is a partially cross-sectional view and partially schematic view of a defect inspection system to illustrate the preferred embodiment of the invention. To simplify FIG. 5A, the two illumination beams 22 and 24, computer 62 and the mechanisms for moving the wafer are not shown in the figure. Radiation scattered by spot 20a on wafer 20 and collected by lens 38 is reflected by mirror 102 to detector 40. Stop 104 blocks the specular reflection of the normal incident beam 22 from detector 40 and results in a cone shape of the convergent beam in FIG. 2. The beam collected and focused by lens 38 and reflected by mirror 102 passes through a beam splitter 106 and a portion of the collected radiation that passes through the beamsplitter is focused onto detector 40 to provide a single output as would be the case in normal SP1$^{TBI}$ operation. Beamsplitter 106 reflects and diverts a portion of the collected radiation from lens 38 to the arrangement 80 of optical fibers of FIG. 4. Preferably, the size of optical fibers 82 and the size of the hollow cone reflected by beamsplitter 106 are such that fibers 82 collect and convey most of the radiation in the hollow cone of radiation. Each of the fibers 82 is then connected to a corresponding detector or a detecting unit in a multi-unit or multi-element detector. In a similar manner, beamsplitter 112 diverts a small portion of the radiation collected by ellipsoidal mirror 52 towards arrangement 70' of optical fiber channels 72, shown more clearly in FIG. 5B, where each channel 72 is connected to a separate detector or a separate detecting unit in a multi-element detector system (not shown). As shown in FIG. 5A, beamsplitter 112 is such that it diverts radiation only within a narrow ring 114 to arrangement 70'. Most of the radiation collected by mirror 52 is passed through beamsplitter 112 and focused to detector 60 to provide a single output as would be the case in normal SP1$^{TBI}$ operation. In FIG. 5A, the illumination beams 22, 24 and the mechanisms for moving the wafer have been omitted to simplify the figure.

As will be evident from a comparison of system 10 of FIG. 1 and system 100 of FIG. 5A, system 100 retains substantially all of the features of system 10 of FIG. 1. In addition, system 100 diverts a portion of the scattered radiation collected by each of lens 38 and mirror 52, and directs them towards fibers 82, 72 to convey the segmented radiation to a separate detectors or detecting units. The system is compact and requires minimal additional space compared to the SP1$^{TBI}$ system 10 of FIG. 1. In this manner, a single combined instrument may be optimized and used for both unpatterned and patterned wafer inspection, thereby eliminating the need for two separate instruments for the two types of wafer inspection.

When only patterned wafers are to be inspected, an alternative defect inspection system 150 of FIG. 6A may be used. In FIG. 6A, the illumination beams 22, 24, computer 62 and the mechanisms for moving the wafer have been omitted to simplify the figure. As shown in FIG. 6A, scattered radiation collected by lens 38 and by mirror 52 are reflected by mirror 112' towards an arrangement of optical fibers 152 which is shown more clearly in cross-section in FIG. 6B. As shown in FIG. 6B, arrangement 152 includes a ring of fibers 82 conveying scattered radiation collected by lens 38 and a ring of fibers 72 conveying scattered radiation collected by mirror 52. As before, each of the fibers 72, 82 are connected to a separate detector or a detecting unit of a multi-unit detector.

While a single ring of detectors are shown in FIGS. 4 and 5B, multiple rings may be employed such as that shown in FIG. 3A. The optically transmissive cores of optical fibers that are located adjacent to each other in each of the two arrangements 70, 70', 80 are separated from each other by the claddings that envelope the cores so that crosstalk between adjacent cores is reduced. Obviously, optical channels other than fibers may be used and are within the scope of this invention. Where such channels do not include separators such as the cladding in the case of optical fibers, other optical separators may be employed to reduce crosstalk.

In reference to FIG. 5A, while the diversion of some of the collected scattered radiation from detectors 40 and 60 may reduce somewhat the particle sensitivity of system 100 when inspecting unpatterned wafers, such reduction is not significant due to the high efficiency of the narrow and wide collection channels of system 100. If desired, when inspecting unpatterned wafers, radiation conveyed by fibers 72 and 82 may be directed towards detectors 40 and 60, respectively, to substantially restore the sensitivity of system 100 so that the resulting sensitivity is substantially the same as that of system 19 of FIG. 1.

Systems 100 and 150 of FIGS. 5A and 6A are particularly advantageous for distinguishing between micro-scratches and particles. The scattering pattern due to a micro-scratch gives the highest concentration of energy and greatest detection uniformity when illuminated normally and captured in the near normal or narrow channel collected by lens 38. The unique signature of the scratch in the form of an elongated pattern in the far-field, allows for a simple method of classification. Therefore, if the eight or more fibers 82 arrange in a ring format is placed in the path of the hollow cone of light focused by lens 38 towards fibers 82 as diverted by beamsplitter 106, where the outputs of these fibers are directed onto a multi-channel detector or an array of individual detectors, by simple process of comparing the signals obtained through any two diagonally opposed fibers relative to the signals in the remaining fibers, the presence of the micro-scratch is obtained. When illuminated obliquely, micro-scratches result in scattering patterns which can be distinguished from those due to particles, by using the multiple detection channels that were described above in conjunction with pattern inspection, viz. multiple fiber units 70 and 70'. In both the wide and narrow channels, it is also possible to place individual detectors or multi-element detecting systems directly in the path of the converging hollow cone of light, rather than individual optical fibers.

Array Wafers

Where systems 100, 150 are used for inspecting wafers with memory cells thereon, the Fourier components from the memory array will spin as the wafer is rotated. These components will thus rotate and be at different azimuthal angles about the normal direction 36 of FIGS. 1, 5A and 6A. This means that these Fourier components will be conveyed by different fibers 72, 82 as the wafer is rotated. Since the array of memory cells may have different dimensions in the X and Y directions of the wafer, as the wafer rotates, the number of detectors that are saturated by the Fourier components will change. This can be provided for by knowing the X and Y dimensions of the memory cells so that the number of Fourier diffraction components can be estimated. Alternatively, during an initialization process at the beginning, a learn cycle is performed where the maximum number of Fourier components that need to be eliminated is determined by noting the maximum number of detectors with very strong, or saturated, outputs. During the subsequent measurement, this number of detector outputs may then be eliminated, where the outputs eliminated are the ones that are saturated or the ones that have the largest values. In the case of a multi-anode PMT, for example, where each anode is used and is connected to a corresponding fiber, cross-talk may be reduced by also eliminating the components adjacent to the detectors having the highest outputs. For example, if the wafer in one position gives three Fourier components, and in another two, the three direct components together with two components adjacent to each would be eliminated for a total of nine detector outputs that are eliminated. This leaves seven useable detector outputs. This number will be maintained regardless of the exact orientation of the wafer. This allows the user to maintain the sizing option for the particles.

Preferably the fibers 72 and 82 are arranged rotationally symmetrically around a direction, such as axes 74 and 84 shown in FIGS. 3A, 4, 5B and 6B. When arranged in such manner, the radiation scattering directions are partitioned into identical angular segments and radiation scattered within each segment is collected by a corresponding fiber. When beamsplitter or mirror 102, 112, 112' reflects or diverts a portion of the radiation collected by lens 38 or mirror 52, the azimuthal positions of the collected scattered radiation is preserved when the reflected or diverted radiation is directed to the fibers 72, 82. When such radiation is so reflected or diverted, axes 74, 84 correspond to the normal direction 36, and the azimuthal positions of the collected scattered radiation about the axes 74, 84 corresponding to their azimuthal positions about the normal direction 36 are preserved.

As described above, azimuthal characterizations of scattered radiation are preserved both for the narrow and the wide channels. The scattering pattern due to a micro-scratch illuminated by beam 22 in a substantially normal illumination direction gives the highest concentration of energy and the greatest detector uniformity when captured in the narrow channel. Furthermore, the unique signature of a scratch in the shape of an elongated pattern in the far-field allows for a simple method of classification. In reference to FIG. 4, for example, when the eight fibers 82 in arrangement 80 are used to receive and carry the scattered radiation in the hollow cone of light of FIG. 2 collected by lens 38, where the fibers are each connected to an individual detector, the sum of the two signals from any two diametrically opposed fibers may be compared with the output signals of the remaining detectors to ascertain the presence of a micro-scratch.

As explained above, if all of the scattered radiation from illuminated spot 20a is collected and directed to a single detector, the presence of Fourier or other scatter components will cause the detector to saturate so that the system will not be able to provide useful information concerning anomalies in the illuminated spot. For this reason, applicants propose segmenting the collected scattered radiation into different segments. If the collected scattered radiation is divided into very few segments, such as two or three, resulting in two or three output signals, the probability may be high that the two or three segments would still contain pattern scatter so that the two or three detectors would again become saturated and yield no useful information concerning anomalies. Thus, to be useful, the segmentation is preferably fine enough that at least some of the detector signals contain no significant pattern scatter. Thus, if lines joining various Fourier or other scatter components to the normal direction 36 do not get closer to each other angularly than δφ, it is preferable for the segmentation to be such that each detector receives scattered radiation collected within an angular aperture of no more than δφ. In this manner, one can be assured that there will be at least some detectors that will receive no Fourier or other pattern scatter and will yield output signals that are useful for ascertaining the presence of, or the characterization of, defects on the sample surface. Where the segmented radiation is conveyed to multiple optical fibers, it is, therefore, preferable for at least some of the fibers to receive radiation collected within azimuthal angles of no more than δφ.

Another arrangement for segmenting the collection of the scattered radiation is illustrated in FIG. 7. FIG. 7 is a top view of a rotationally symmetric collector such as an ellipsoidal or paraboloidal mirror 200 with two apertures 202, 204, where the two apertures are preferably centered at +90 and −90 azimuthal positions relative to the oblique beam 24 illustrated in FIGS. 1 and 7. A multi-element detector or detector array 206, 208, is placed in each of the two apertures, where the detector or array may be a multi-anode PMT or multi-PIN diode array. FIG. 8A is a schematic side view of a portion of the detector or detector array 206, 208 of FIG. 7 along arrow 8A. As shown in FIG. 8A, each of the detecting units 206a, 208a has a substantially rectangular shape, with width w. Preferably, the units 206a, 208a are arranged substantially with their elongated sides parallel to the normal direction 36. In this manner, each of the detecting units 206a, 208a collects scattered radiation within a small angular sector subtended by the widths of the elongated elements 206a, 208a towards the center axis 36 where the angle of such sector subtended is no more than δφ, so that at least some of the detectors would provide useful signals for detecting and characterizing anomalies on the sample surface without being masked by pattern scatter.

By placing two detector or detector arrays 206, 208 at the apertures 202, 204, respectively, the detector units 206a, 208a will provide useful signal components for detecting anomalies. The above-described process of either estimating or determining through a quick learn cycle may be applied to the two detector or detector arrays 206, 208 for ascertaining the maximum number of pattern scatter components that need to be eliminated, so that the remaining detector signals can then be used for detecting anomalies.

The size of the semiconductor circuits is continually being reduced. Thus, when the cell size is reduced, this correspondingly reduces the number of Fourier or other scatter components. For larger cell sizes, if the width w of the detecting units of detectors or detector arrays 206, 208 are not reduced, each of the detecting units in the two detectors or detector arrays 206, 208 will become saturated so that again no useful signal results. This can be remedied by the scheme illustrated in FIG. 8B.

It is possible to further enhance the signal gathering capability of the detectors or detector arrays 206, 208 as illustrated in FIG. 8B. In the event that the number of pattern scatter increases beyond what the detectors or detector arrays were designed for, using the arrangement of FIG. 8B allows anomaly detection despite such increase. As shown in FIG. 8B, the multiple detecting units of detectors or the detector arrays 206, 208 are labeled from the same side to the other; D1, D2 . . . D2n, D2n+1 . . . The odd numbered detecting units D1, D3, D5 . . . D2n+1 . . . of multi-unit detector or detector array 206 are masked by a spatial filter 216. The even numbered detecting units D2, D4, D6 . . . D2n . . . of detector or array 208 are masked by a spatial filter 218 as shown in FIG. 8B. In this manner, as relative rotation motion is caused between the sample surface and detectors or arrays 206, 208, the detecting units that are not covered would still provide useful signals.

FIG. 9A is a cross-sectional view of collector 52 of FIG. 1 modified to include the type of apertures or detector or detector arrays illustrated in FIGS. 7, 8A and 8B. The two apertures 202, 204 are, preferably, of a size such that each aperture comprises an azimuthal gap of about 10°–40° on each side centered on ±90° azimuth. The apertures are located only towards the bottom portion of the collector so that only scattered radiation along directions close to the surface are detected by the detectors or detector arrays 206, 208. Two lenses 222, 224 with the appropriate F numbers are used for collecting and focusing the scattered radiation from the illuminated spot 20a to their respective detector or detector array 206, 208. The two detector or detector arrays may be placed at the back focal planes of the two lenses 222, 224.

The masks 216, 218 may be placed between the illuminated spot 20a and the detectors or detector arrays 206, 208 by means of filter wheels 226, 228 rotated by actuators 232, 234 in a manner known to those skilled in the art so that the connections between these two actuators and the wheels are not shown and a detailed description of their operation is not necessary herein. For simplicity, only the mask portions 216, 218 of the two filter wheels 226, 228 are illustrated in FIG. 9A. The features illustrated in FIGS. 9A, 9B and 9C may be combined with the systems 100, 150 of FIGS. 5A and 6A to further increase their versatility. When the combined instrument is used for the inspection of unpatterned or bare wafers, for example, reduction in sensitivity due to the two apertures 202, 204 is not significant. Furthermore, the outputs of detectors or detector arrays 206, 208 can obviously be added to the output of detector 60 at least partially to restore the sensitivity of the system when inspecting unpatterned wafers. To suppress extraneous signals caused by film roughness, the feature of FIGS. 9A–9C may be advantageously used as well. Since film roughness scatters P-polarized light more efficiently than S-polarized light, in such circumstances, it will be desirable to supply an oblique illumination beam 24 which is S-polarized, and collect only the S-polarized scatter from illuminated spot 20a. This may be accomplished conveniently by means of filter wheels 226, 228. Actuators 232, 234 may be used to rotate the filter wheels 226, 228 so that a S-polarizer 236 would take the place of mask 216 and another S-polarizer would take the place of mask 218 in FIG. 9A. As will be noted from FIG. 9A, this arrangement is advantageous since the two filters 236, 238 are located close to the surface of wafer 20 so that the collected radiation is confined to scattering angles that are very close to the wafer surface. In the case of very rough films, to further restrict the collection elevation angles, the upper half of the S-polarizer may be blocked by using the semi-circular opaque screen 236', 238' in the filter wheel. For example, the semi-circular S-polarizer may restrict the elevational collection angles of the aperture to within a range of about 55 to 70° from the normal direction 36. This is helpful since the amount of scatter caused by film roughness increases with the elevation angles to the wafer surface. FIG. 9C illustrates an alternative filter wheel that may be used for the inspection of bare or unpatterned wafers.

If the directions of the expected pattern scatter surface are known, spatial filters may be designed to block such scattering, thereby detecting only the scatter by anomalies on the surface. FIG. 10 is a schematic view illustrating the two-dimensional Fourier components of an array structure when illuminated with normal incidence radiation. As the sample rotates, all of the spots at the intersections of the X-Y lines will rotate, thereby generating circles. These circles represent the loci of the Fourier components as the wafer is rotated. The dark opaque circle at the center is the 0–5° blockage of the collection space caused by stop 104 in FIG. 5A. From FIG. 10, it is noted that there are gaps in between the circles where there are no Fourier components. At least in theory, it is possible to construct a programmable filter (e.g. a liquid crystal filter) in which annular bands of arbitrary radii are blocked out. A simple spatial filter may be constructed also to achieve many of the objectives herein. Thus, if the cell size of a regular memory array on the wafer is such that its X and Y dimensions are not larger than about 3.5 microns, for example, this means that for 488 nanometers wavelength radiation used in the illumination beams 22, 24, the first Fourier component is at about 8° to the normal direction 36. Therefore, if a spatial filter is employed, blocking all collected radiation in the narrow channel that is at 8° or more to the normal direction 36 will leave an annular gap of 2 or 3° ranging from the rim of the central obscuration (i.e. 5 or 6°) to the rim of the variable aperture at about 8°. Under these conditions, as the wafer spins, no Fourier components can possibly get through the annual gap and scatter from the array is suppressed. In one embodiment, the spatial filter used leaves an annular gap between about 5 to 9° from the normal direction 36.

In the example above, a spatial filter is designed for the narrow channel; it will be understood that similar spatial filters may be designed for the wide channel as well. Such and other variations are within the scope of the invention.

As explained above, in order to assure that at least some detectors will receive useful signals that are not masked by Fourier or other pattern scatter, the collection aperture of at least some of the detectors are preferably no larger than the angular separation between the expected pattern scatter. For this purpose, a spatial filter may be constructed where all of the collected radiation in the narrow or wide channel is blocked except for a small angular aperture where the angle of the angular aperture is not larger than the angular separation between pattern scatter. When such a spatial filter is placed between illuminated spot 20a and the detector, such as detector 40 or 60, the Fourier components will spin in and out of this little opening. When there is no component going through, the data will be valid for detection of anomalies. Otherwise, the signal will be very strong, or even saturated. Thus, at the end of the spiral scan, the wafer map will be a series of data-valid, and saturated sectors. If the scan is repeated a second time where the center position of the angular aperture is shifted relative to its position during the first scan by the minimum angular separation of the patterned scatter, one would again obtain a similar map comprising data-valid and saturated sectors as before. However, in those areas that were saturated during the first scan, one now has valid data. Therefore, by combining the two data sets using the logical OR operation, a full wafer map of valid data can be achieved.

The above process can be simplified by employing an asymmetric mask 250 illustrated in FIG. 11. As shown in FIG. 11, the two sector shaped apertures 252, 254 are offset from a diametrically opposite position by an angle which is equal to the expected minimum angular separation of pattern scatter. When such a filter is placed between the illuminated spot 20a and detector 40 or 60 of FIG. 1, the detectors 40 and 60 will then provide a full wafer map when the wafer is scanned.

FIG. 12 is a schematic view of a defect detection system illustrating another alternative embodiment of the invention. As shown in FIG. 12, when illuminated by beams (not shown), such as beams 22, 24 of FIG. 1, the scattered radiation collected by collector 52 (omitted from FIG. 12 to simplify the figure) are focused to a triangular-shaped device 262 having two mirrors 262a, 262b on opposite sides of the device. The illumination beams have also been omitted for simplicity. The scattered radiation are, therefore, reflected into two opposite hemispheres by device 262. Mirror 262a reflects half of the scattered radiation towards PMT1 and mirror 262b reflects the other half of scattered radiation towards PMT2 and asymmetric mask 250 may be employed between mirror 262a and PMT1 and between mirror 262b and PMT2. In this manner, the two PMTs will provide two wafer maps useful for anomaly detection and classification.
Detection of CMP Defects One aspect of this invention covers two algorithms for classifying CMP defects. The first method is based on the spatial distribution of the light scattered by defects. Theoretical simulation and experimental results indicate that the light scattered by CMP micro-scratches is primarily in the direction of specular reflection while light scattered by particles (especially, small particles) has a different spatial distribution. As a result, defect classification can be achieved by measuring the distribution of the scattered light. It can be implemented by using two or more detectors placed at proper positions, around the scatterers. Or, using one detector with two or more spatial filters/masks. Three different ways of implementing this algorithm are set forth below.

The second algorithm is based on a dual-polarization method. This method compares the scattering signal from a defect using incident S and P polarized beams. Theoretical simulation indicates that the scattering intensity is proportional to the local interference intensity seen by the defects. This interference intensity is different for S and P polarized light and has a dependence on the height above the wafer surface. Thus, the interference intensity seen by a particle (an above-surface defect) is very different from that seen by a micro-scratch (at or below the wafer surface). Defect classification can be achieved by comparing the scattering signal strength using both S and P polarized incident light or radiation.

Details of Operations

In the following paragraphs, we describe the implementations/operations of the inventions in a Surfscan SP1$^{TBI}$ system. However, the algorithms are not limited to the SP1$^{TBI}$ system. They can be implemented in any optical scattering tool. For all the algorithms described below, PSL calibration curves for all the utilized channels are required. They are crucial to the success of the classification of CMP defects.

Algorithm#1, Implementation#1, Dual-channels, Oblique Incidence and One Scan

There are four dark field channels in an SP1 system: DWN, DNN, DWO and DNO, where DWN stands for the channel carrying scattered radiation collected by the ellipsoidal mirror originating from a normal illumination beam, DNN for the channel carrying scattered radiation collected by the lens collector originating from a normal illumination beam, DWO for the channel carrying scattered radiation collected by the ellipsoidal mirror originating from an oblique illumination beam, and DNO for the channel carrying scattered radiation collected by the lens collector originating from an oblique illumination beam. The dual-channel method uses two dark-field channels, for example the DWO and the DNO channels. The principle of this method is based on the fact that particles and micro-scratches have different spatial scattering patterns. A particle scatters light in all directions, which can be collected by both dark-field channels. However, a micro-scratch preferentially scatters light in certain directions, resulting in the signal captured in one channel being significantly larger than that in the other channel. For example, when the oblique channels DWO and DNO are used, micro-scratches are preferentially captured in the DWO channel or the signal in DWO channel is significantly larger than that in DNO channel. To differentiate micro-scratches from particles, we calculate the size ratio of each defect captured in DWO and DNO channels. If the size ratio for a defect is close to one, it is classified as a particle. However, if the size ratio of a defect is less than certain fraction number (example: 0.8), it is classified as a micro-scratch. If a defect is only captured in DWO channel but not in DNO channel, it is classified as a CMP micro-scratch. If a defect is only captured in DNO channel but not in DWO channel, it is classified as a particle.

Algorithm#1, Implementation#2, Dual-channels, Normal Incidence and One Scan

The implementation in normal channels is similar to that in oblique channels. The difference is that the light scattered from a CMP micro-scratch is preferentially towards narrow channel (DNN) in normal incidence instead of wide (DWN) channel. This is consistent with the fact that CMP micro-scratches scatter light preferentially towards the direction of specular reflection. The defect classification is achieved by calculating the size ratio of a defect captured in both DNN and DWN channels. If the size ratio for a defect is close to one, it is classified as a particle. However, if the size ratio of a defect is larger than certain number (example: 1.6), it is classified as a micro-scratch. If a defect is only captured in DNN channel but not in DWN channel, it is classified as a CMP micro-scratch. If a defect is only captured in DWN channel but not in DNN channel, it is classified as a particle.

Algorithm#1, Implementation#3, Single-channel, Oblique Incidence, Two Masks and Dual-scans The third method of implementing algorithm #1 uses two masks. One of the masks (#1) is designed to capture preferentially the scatter from CMP micro-scratches; this mask is illustrated in FIG. 13A, where the shaded region indicates the area where radiation is blocked, and the non-shaded region indicates the area where radiation transmittance is allowed. The other one (#2) is designed to block the light scattered by CMP micro-scratches; this mask is illustrated in FIG. 13B, where the shaded region indicates the area where radiation is blocked, and the non-shaded region indicates the area where radiation transmittance is allowed. The calibration curves of both mask configurations are needed. The defect classification is achieved by calculating the size ratio of a defect captured in both mask configurations. For a given defect, if the size ratio of mask#1 and mask#2 is close to one, it is classified as a particle. However, if the size ratio of a defect is larger than certain number (example: 1.15), it is classified as a micro-scratch. If a defect is only captured in mask#1 configuration but not in mask#2 configuration, it is classified as a CMP micro-scratch. If a defect is only captured in mask#2 configuration but not in mask#1 configuration, it is classified as a particle.

Algorithm #1 can also be implemented with a multi-anode PMT. The advantage of this method is that it can be done in one scan. It is essentially the same as using two masks, but only one scan is needed for data collection.

Algorithm #2, Implementation#1, Single-channel, Dual-polarizations, Oblique Incidence and Dual Scan Algorithm#2 utilizes two incident polarizations, S and P. Two scans are needed for this method. One is for S-polarization; the other is for P-polarization. The PSL calibration curves for both S- and P-polarizations are used. The defect classification is achieved by calculating the size ratio of a defect captured in both P and S scans. If the size ratio of P and S scans is close to one, it is classified as a particle. However, if the size ratio of a defect is other than one (example: <0.65 or >1.85 depending on film thickness), it is classified as a micro-scratch. For a dielectric film, the interference intensity for the two polarizations will vary with film thickness. The changes in interference intensity of the two polarizations are out of phase; when the P polarization interference intensity is at a maximum, the S polarization interference intensity will be at a minimum and vice versa. Thus, the size ratio for CMP defects will either be greater or less than 1.0 depending upon the thickness of the dielectric film. Similarly, if a defect is captured only in one polarization but not the other, it is classified as a CMP micro-scratch or particle depending on the film thickness. This method has been successfully demonstrated using oxide CMP wafers. This method is expected to work better for metal films than thick dielectric films since thickness variation across the wafer is not a concern for most metal film with practical thicknesses.

In one experiment, the SP1$^{TBI}$ instrument is calibrated using PSL spheres so that the size ratio of the detected intensities during the P and S scans is normalized to 1 for particles. Thus, the particles present would give rise to ratios at or around 1. In addition, from a histogram provided by the instrument, a second set of intensity ratios clusters at a value greater than 1, indicating a set of defects that scatter more in response to P-polarized illumination than S-polarized illumination. These are CMP defects such as micro-scratches; this would be true even where scattered intensities are detected only during the P scan and not during S scan since in that instance the ratio is infinite and therefore greater than 1. A third group of ratios are at zero or close to zero values. These are deemed to indicate particles, for the reasons explained below.

Interference effects at the surface inspected when illuminated by P- or S-polarized radiation cause the scattered intensity detected to be stronger during a P scan compared to that during a S scan, or vice versa. Thus, in the experiment above, if the interference effects at the surface are such as to cause the scattered intensity detected to be stronger during a P scan compared to that during a S scan, only particles large enough will be in a region where S polarization is experiencing constructive interference. This is illustrated, for example, in FIG. 14. For example, in reference to FIG. 14, if the film thickness at the wafer surface is 200 nanometers, from the curves in FIG. 14, one would expect the interference intensity at the wafer surface to be much stronger when illuminated by P-polarized radiation then when it is illuminated by S-polarized radiation. However, particles 300 nanometers or above would cause the scattered intensity detected during a S scan to be much stronger than that during a P scan.

Surface Roughness Determination

For opaque films such as metals and transparent dielectrics such as dielectrics with low k (both spun on a CVD deposited), haze measured from the films varies with surface roughness of the films if there is little film thickness variation. Most dielectric films CVD deposited for integrated circuit applications are quite uniform. Hence, haze measurements may provide a quick alternative to the measurement of film roughness.

Surface roughness is typically measured by instruments such as the HRP® tool from KLA-Tencor Corporation of San Jose, Calif., and atomic force microscope or any other type of scanning probe microscopes such as near field microscopes or scanning tunneling microscopes. Such a process is slow. By making use of the above relationship that haze has with film roughness for uniform dielectric films, or metals of a wide variety of uniformity film roughness can be measured much more quickly than conventional methods. Thus, in reference to FIG. 16, a database may be constructed by measuring surface roughness of representative films 302 of different thicknesses using the KLA-Tencor High Resolution Profiler, or AFM type tool 304, and measuring haze values of these same films using the SP1$^{TBI}$ system 10, or one of the combined systems (e.g. 100) described above or any other tool that can be used to measure haze, in order to build a database using computer 310 of the correlation between haze and surface roughness for films of different thicknesses. Measurement of like films of various thicknesses may be preferable since surface roughness increases with film thickness. A database may then be constructed such as the graphical plot shown in FIG. 15. Then if it is desirable to determine the surface roughness of an unknown film, its roughness may be determined by measuring the haze of the film using an instrument such as system 10 of FIG. 1 or the combined instruments described above. The haze measurement is then used to select a corresponding roughness value from the database for a film of known thickness, such as from the graph shown in FIG. 15. This will save the end user in the fabrication facility up to an hour for each film since it takes only about one minute to measure the haze value and correlate the haze measurement with the RMS roughness calibration curve of FIG. 15.

While the invention has been described above by reference to various embodiments, it will be understood that changes and modifications may be made without departing from the scope of the invention, which is to be defined only by the appended claims and their equivalents. All references mentioned herein are incorporated in their entireties by reference.

What is claimed is:

1. A method for determining roughness of a surface, comprising:

providing a database correlating haze values with surface roughness of thin films;

measuring a haze values of the surface; and determining a roughness value of the surface from the haze value and the database, wherein said providing includes measuring surface roughness values and haze values of representative thin films and building the database using such values from the representative thin films.

2. The method of claim 1, said providing further including:

compiling said database.

3. The method of claim 1, wherein said roughness values measuring is performed by means of a profilometer or a scanning probe microscope.

4. A system for determining roughness of a sample surface, comprising:

a device measuring surface roughness values and haze values of representative thin films and building a database using such values from the representative thin films, said database correlating haze values with surface roughness of thin films;

an instrument measuring one or more haze values of the sample surface; and means for determining one or more roughness values of the sample surface from the one or more haze values of the sample surface and the database.

5. The system of claim 4, said device comprising a profilometer or a scanning probe microscope that measures surface roughness values of representative thin films.

* * * * *